United States Patent [19] | [11] Patent Number: 4,937,242
Matsui et al. | [45] Date of Patent: Jun. 26, 1990

[54] 1,4-DIHYDROPYRIDINE DERIVATIVES AND PHARMACEUTICAL COMPOSITION THEREOF

[75] Inventors: Hiroshi Matsui, Nara; Fumio Fukata, Mukoh; Takayoshi Mori, Kyoto; Nobuharu Kakeya, Nagaokakyo; Kazuhiko Kitao, Kyoto, all of Japan

[73] Assignee: Kyoto Pharmaceutical Industries, Ltd., Kyoto, Japan

[21] Appl. No.: 165,705

[22] Filed: Mar. 8, 1988

Related U.S. Application Data

[63] Continuation-in-part of Ser. No. 162,494, Feb. 23, 1988, abandoned.

[30] Foreign Application Priority Data

Mar. 12, 1987 [JP] Japan .................................. 62-57717

[51] Int. Cl.[5] .................... A61K 31/495; A61K 31/44; A61K 31/445; A61K 31/535; C07D 401/06; C07D 401/14

[52] U.S. Cl. ................................ 514/235.8; 514/218; 514/252; 514/318; 514/341; 540/575; 544/121; 544/124; 544/130; 544/139; 544/360; 544/364; 546/193; 546/194; 546/278

[58] Field of Search ................ 540/575; 544/360, 121, 544/124, 130, 139, 360, 364; 546/276, 278, 193, 194; 514/218, 252, 341, 235.8, 340, 318

[56] References Cited

U.S. PATENT DOCUMENTS

| | | | |
|---|---|---|---|
| 3,905,983 | 9/1975 | Bossert et al. | 546/321 |
| 3,950,336 | 4/1976 | Meyer et al. | 546/257 |
| 3,951,991 | 4/1976 | Meyer et al. | 546/257 |
| 3,951,993 | 4/1976 | Meyer et al. | 546/257 |
| 3,959,296 | 5/1976 | Bossert et al. | 546/321 |
| 4,031,104 | 6/1977 | Bossert et al. | 546/257 |
| 4,044,141 | 8/1977 | Bossert et al. | 546/257 |
| 4,048,171 | 9/1977 | Bossert et al. | 546/257 |
| 4,430,333 | 2/1984 | Campbell et al. | 544/360 |
| 4,532,248 | 7/1985 | Franckowiak et al. | 546/286 |
| 4,548,935 | 10/1985 | Aeker et al. | 544/360 |
| 4,603,135 | 7/1986 | Meguro et al. | 544/360 |
| 4,656,181 | 4/1987 | Sunkel et al. | 546/321 |
| 4,727,066 | 2/1988 | Sunkel et al. | 544/364 |
| 4,739,106 | 4/1988 | Miyano et al. | 548/300 |

FOREIGN PATENT DOCUMENTS

| | | | |
|---|---|---|---|
| 60674 | 9/1982 | European Pat. Off. | 544/360 |
| 68259 | 1/1983 | European Pat. Off. | 544/360 |

OTHER PUBLICATIONS

Bossert et al., Chem. Abst. 80-14958g (19), "Coronary Dilating 1,4-Dihydropyridine-3,5-Dicarboxylates".

Yamanouchi Pharm. Co. Ltd., Chem. Abst. 97-127516f (1982), "Aminoalkyl 5-Alkanoyl-1,4-Dihydropyridine-3-Carboxylates".

Araki et al., Chem. Abst. 100-85591z (1984), "1,4-Dihydropyridine-3,5-Dicarboxylic Acid Ester Derivatives".

Meguro et al., Chem. Abst. 100-209872p (1984), "Dihydropyridine Derivatives and Their Use".

Meguro et al., Chem. Abst. 100-120900y (1984), "Dihydropyridine Derivatives".

Zumin Tricerri et al., Chem. Abst. 101-55114z (1984), "Dihydropyridines with an Antagonistic Activity to Calcium".

Sunkel et al., Chem. Abst. 101-191700q (1984), "1,4-Dihydropyridines Esters and Drugs Containing These Esters".

Takeda, Chem. Ind. Htd. Chem. Abst. 103-87773w (1985), "Dihydropyridine Derivatives".

Tamada et al., Chem. Abst., vol. 104-19517m (1986), "Dihydropyridine derivatives and their Salts".

Meguro et al., Chem. Abst. 104-180214v (1986), "A Pyridine Derivative for Treatment of Arteriosclerosis".

Poindexter et al., Chem. Abst. 104-88595x, "Dihydropyridinyl Dicarboxylic Acid Piperazinyl Derivatives . . . ".

(List continued on next page.)

*Primary Examiner*—Cecilia Shen
*Attorney, Agent, or Firm*—Berman, Aisenberg & Platt

[57] ABSTRACT

1,4-Dihydropyridine derivatives of the general formula:

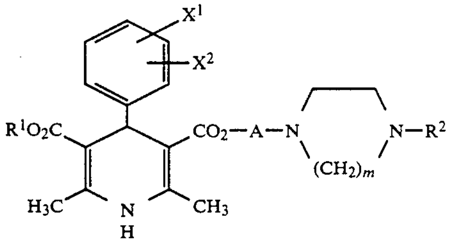

wherein $X^1$ and $X^2$ independently represent hydrogen, fluoromethyl, fluoromethoxy, halogen, cyano, or nitro; $R^1$ represents a lower alkyl; $R^2$ represents acyl, alkoxycarbonyl, acylalkyl, an N-alkyl-substituted carbamoylalkyl, alkoxyalkyl, alkoxycarbonylalkyl, acyloxyalkyl, nitratoalkyl, cyanoalkyl, heterocycle-alkyl, haloalkyl, alkenyl, or alkynyl; A represents an alkylene comprising a carbon atom to which 2 alkyls are bonded and having in total at least 5 carbon atoms; m represents the integer 1, 2 or 3; acid addition salts thereof; a method of production thereof; and pharmaceutical compositions containing such compound(s).

Such compounds have pharmacological activities, in particular potent and long lasting hypotensive activity, coronary vasodilatation, cerebral vasodilatation, peripheral vasodilatation, renal vasodilatation and platelet aggregation inhibitory activity.

11 Claims, No Drawings

OTHER PUBLICATIONS

Ulrich et al., Chem. Abst. 105–226650k (1986), "Piperazine Derivatives".
Meguro et al., Chem. Abst. 105–133842j, "New 1,4–Dihydropyridine Derivatives with Potent and Long–Lasting Hypotensive Effect".
Kitagawa et al., Chem. Abst. 106–67128y, "1,4–Dihydropyridine Derivatives".
Sugano et al., Chem. Abst. 106–32851b (1987), "1,4–Dihydropyridine Derivatives".
Leonardi et al., Chem. Abst. 107–175780j (1987), "Preparation of Pyridinylflavone . . . ".
Nakaya et al., Chem. Abst. 108–124246c (1988), "Cardiac Versus Vascular Effects of a New Dihydropyridine Derivatives, CV–4093".
Stanton et al., Chem. Abst. 108–216042m (1988).
Okabe et al., Chem. Abst. 108–49001p (1988).

1,4-DIHYDROPYRIDINE DERIVATIVES AND PHARMACEUTICAL COMPOSITION THEREOF

This application is a continuation-in-part of application Ser. No. 162,494, filed February 23, 1988 and now abandoned.

FIELD OF THE INVENTION

The present invention relates to new 1,4-dihydropyridine derivatives which are useful as pharmaceuticals and acid addition salts thereof.

BACKGROUND OF THE INVENTION

It is known that some 1,4-dihydropyridine compounds possess coronary artery dilating activity and/or vasodepressor activity.

In fact, however, it is difficult to say that synthesis and pharmaceutical studies of such 1,4-dihydropyridine derivatives have given satisfactory results.

The present inventors made studies with the aim of developing new 1,4-dihydropyridine derivatives which possess very excellent pharmacological activities, in particular potent and long lasting hypotensive activity, coronary vasodilatation, cerebral vasodilatation, peripheral vasodilatation, renal vasodilatation and platelet aggregation inhibitory activity and which are of low toxicity; as a result, the inventors discovered new compounds which possess these activities and which are of low toxicity, and completed the present invention.

SUMMARY OF THE INVENTION

The present invention relates to 1,4-dihydropyridine derivatives represented by the general formula:

(I)

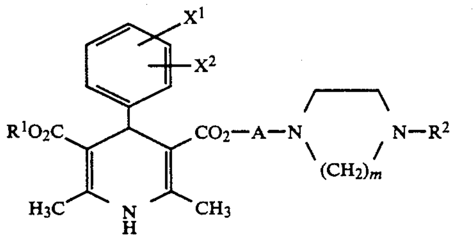

wherein $X^1$ and $X^2$ independently represent hydrogen, fluoromethyl, fluoromethoxy, halogen, cyano, or nitro; $R^1$ represents a lower alkyl; $R^2$ represents acyl, alkoxycarbonyl, acylalkyl, an N-alkyl-substituted carbamoylalkyl, alkoxyalkyl, alkoxycarbonylalkyl, acyloxyalkyl, nitratoalkyl, cyanoalkyl, heterocycle-alkyl, haloalkyl, alkenyl, or alkynyl; A represents an alkylene comprising a carbon atom to which 2 alkyls are bonded and having in total at least 5 carbon atoms; m represents the integer 1, 2 or 3, [hereinafter also referred to as Compound (I)] or to acid addition salts thereof.

DETAILED DESCRIPTION OF THE INVENTION

In the present specification, $C_x$ means that the number of carbon is x; for example, $C_{1-4}$ means that the number of carbon is 1 to 4.

The substituents represented by $X^1$ and by $X^2$ in this specification are independently hydrogen, fluoromethyl (e.g. difluoromethyl, trifluoromethyl), fluoromethoxy (e.g. monofluoromethoxy, difluoromethoxy), halogen (e.g. chlorine atom, bromine atom, fluorine atom), cyano or nitro.

The lower alkyl represented by $R^1$ in this specification may be linear, may be branched or may be cyclic, and lower alkyls having 1 to 4 carbons, such as methyl, ethyl, n-propyl, isopropyl, n-butyl, isobutyl, sec-butyl and cyclopropylmethyl are preferred.

The acyl represented by $R^2$ in this specification may be an aliphatic acyl, may be an aromatic acyl, or may be a heterocyclic acyl. The aliphatic acyl may be linear, or may be branched. The preferable number of carbons is 1 to 5. When the aliphatic acyl is unsaturated, it is preferable that the aliphatic acyl has 1 to 2 double or triple bonds. The aromatic acyl or heterocyclic acyl may be any of those in which a carbonyl group is bonded directly to an aromatic group or heterocyclic group and those in which a carbonyl group is bonded to an aromatic group or heterocyclic group via aliphatic group (e.g. a saturated or unsaturated aliphatic group having 1 to 3 carbons, and, when it is unsaturated, having 1 to 2 double or triple bonds). For the heterocycle, 5- or 6-membered heterocycles, specifically those whose heteroatom is a nitrogen atom or an oxygen atom are preferred. The aliphatic group, aromatic group and hetero cyclic group in the aliphatic acyl, aromatic acyl and heterocyclic acyl may be substituted by halogen (chlorine atom, bromine atom, etc.), hydroxyl group, carboxyl group, alkoxy group, acyl group, acylamino group, etc., and the acyl in the substituent acyl group or acylamino group is exemplified by the same acyls as those mentioned above.

As specific examples of appropriate acyls represented by $R^2$, mention may be made of formyl, acetyl, crotonoyl, acryloyl, propioloyl, benzoyl, phenylacetyl, cinnamoyl, p-acetaminobenzoyl, m-methoxybenzoyl, m-dimethylaminobenzoyl, p-hydroxycinnamoyl, p-acetaminobenzoyl, furoyl, nicotinoyl, and piperidinomethylcarbonyl.

The alkoxycarbonyl may be any alkoxycarbonyl having a linear or branched $C_{1-5}$ alkoxy, and as specific examples of appropriate alkoxycarbonyls, mention may be made of methoxycarbonyl, ethoxycarbonyl, propoxycarbonyl, and tert-butoxycarbonyl.

The acyl for the acylalkyl is exemplified by the acyls mentioned above, and the alkyl for the acylalkyl is exemplified by linear or branched $C_{1-5}$ alkyls. As specific examples of appropriate acyls and alkyls, mention may be made of phenacyl, acetonyl, methylcarbonylethyl, and pyrrolidinocarbonylmethyl.

The N-alkyl-substituted carbamoylalkyl may be monosubstituted, or may be disubstituted. Both alkyls are independently exemplified by linear or branched $C_{1-5}$ alkyls. As specific examples of appropriate N-alkyl-substituted carbamoylalkyls, mention may be made of methylcarbamoylmethyl, piperazinocarbonylmethyl, and dimethylcarbamoylmethyl.

The alkoxy and alkyl for the alkoxyalkyl are respectively exemplified by linear or branched $C_{1-5}$ alkoxys and $C_{1-5}$ alkyls. As specific examples of appropriate alkoxys and alkyls, mention may be made of methoxyethyl, ethoxyethyl, and methoxypropyl.

The alkoxy and alkyl for the alkoxycarbonylalkyl are respectively exemplified by linear or branched $C_{1-5}$ alkoxys and $C_{1-5}$ alkyls. As specific examples of appropriate alkoxycarbonylalkyls, mention may be made of methoxycarbonylmethyl, ethoxycarbonylmethyl, and ethoxycarbonylethyl.

The acyl for the acyloxyalkyl is exemplified by the acyls mentioned above, and the alkyl for the acyloxyalkyl is exemplified by linear or branched $C_{1-5}$ alkyls. As specific examples of appropriate acyloxyalkyl, mention may be made of acetoxyethyl and benzoyloxyethyl.

The alkyl for the nitratoalkyl is exemplified by linear or branched $C_{1-5}$ alkyls. As specific examples of appropriate nitratoalkyls, mention may be made of nitratoethyl and nitratopropyl.

The alkyl for the cyanoalkyl is exemplified by linear or branched $C_{1-5}$ alkyls. As specific examples of appropriate cyanoalkyls, mention may be made of cyanomethyl and cyanoethyl.

For the heterocycle in the heterocycle-alkyl, 5- or 6-membered heterocycles, specifically those whose heteroatom is a nitrogen atom or an oxygen atom are preferred, and specific examples of such heterocycles include piperidino and morpholino. The alkyl for the heterocycle-alkyl is exemplified by linear or branched $C_{1-5}$ alkyls. As specific examples of appropriate heterocycle-alkyl combinations, mention may be made of piperidinoethyl and morpholinoethyl.

The halogen for the haloalkyl is exemplified by fluorine atom, chlorine atom, bromine atom, etc., and the alkyl for the haloalkyl is exemplified by linear or branched $C_{1-5}$ alkyls. As specific examples of appropriate haloalkyls, mention may be made of trihalogen-substituted methyls (e.g. trifluoromethyl) and halogen-substituted ethyls (e.g. monofluoroethyl).

The alkenyl and alkynyl are respectively exemplified by linear or branched $C_{2-5}$ alkenyls and $C_{2-5}$ alkynyls, such as vinyl, propenyl, isopropenyl, butenyl, ethynyl, propynyl, and pentinyl.

The alkylene comprising a carbon atom to which 2 alkyls are bonded and having in total at least 5 carbon atoms, represented by A in this specification may be linear, or may be branched, and it is preferable that the alkylene be of not more than $C_{10}$, specifically not more than $C_8$. The alkylene is specifically exemplified by 2,2-dimethyltetramethylene, 2,2-dimethylpentamethylene, 2,2-dimethylhexamethylene, 2,2-dimethyltrimethylene, and 1,1-dimethyltrimethylene. As an example of preferable alkylene, mention may be made of 2,2-dimethyltrimethylene.

As stated above, m represents the integer 1, 2, or 3. It is preferable that m be the integer 1 or 2.

The acid addition salt of Compound (I) of the present invention are not subject to any particular limitation, as long as they are pharmacologically acceptable salts, and they are exemplified by salts of inorganic acids (e.g. hydrochlorides, hydrobromides, phosphates, sulphates) and salts of organic acids (e.g. acetates, succinates, maleates, fumarates, malates, tartrates, methanesulfonates).

The 1,4-dihydropyridine derivative (I) of the present invention and its acid addition salts possess very potent and persistent pharmacological activities. In particular, the 1,4-dihydropyridine derivative (I) represented by the general formula (I) in which $R^2$ is acylalkyl, N-alkyl-substituted carbamoylalkyl, alkoxyalkyl, cyanoalkyl, heterocyle-alkyl, alkenyl or alkenyl (in particular, $R^2$ is alkenyl, alkynyl or fluorine-substituted alkyl) or its acid addition salts possess potent and persistent activities, and in addition, are especially excellent in water solubility. Therefore, said derivatives or their acid addition salts can be prepared as drugs which are clinically very easy to handle; for example, they can be formed into eye drops, nasal drops, inhalations, etc., and, in addition, they can be formed into injections of any desired concentration simply by dissolving them in distilled water for injection. Moreover, even if possessing potent activities, any slightly water-soluble 1,4-dihydropyridine compound is undesirable for therapeutic use since its absorbability varies among patients, while the water-soluble 1,4-dihydropyridine derivative (I) of the present invention is particularly excellent since there is hardly any patient-to-patient variation in its absorption and therefore it not only provides desirable drug effects but also enables the easier formation of a therapeutic design according to patients.

As the 1,4-dihydropyridine derivative (I) of the present invention and acid addition salts thereof, there may be mentioned, for example, the following compounds:

*3-(4-Allyl-1-piperazinyl)-2,2-dimethylpropyl methyl 2,6-dimethyl-4-(m-nitrophenyl)-1,4-dihydropyridine-3,5-dicarboxylate dihydrochloride

*3-[4-(2-Propenyl)-1-piperazinyl]-2,2-dimethylpropyl methyl 2,6-dimethyl-4-(m-nitrophenyl)-1,4-dihydropyridine-3,5-dicarboxylate dihydrochloride

*3-(4-Cyanomethyl-1-piperazinyl)-2,2-dimethylpropyl methyl 2,6-dimethyl-4-(m-nitrophenyl)-1,4-dihydropyridine-3,5-dicarboxylate dihydrochloride

*3-[4-(2-Methyl-2-propenyl)-1-homopiperazinyl]-2,2-dimethylpropyl methyl 2,6-dimethyl-4-(m-nitrophenyl)-1,4-dihydropyridine-3,5-dicarboxylate dihydrochloride

*3-(4-Allyl-1-homopiperazinyl)-2,2-dimethylpropyl methyl 2,6-dimethyl-4-(m-nitrophenyl)-1,4-dihydropyridine-3,5-dicarboxylate dihydrochloride

*3-[4-(tert-Butyloxycarbonyl)-1-homopiperazinyl]-2,2-dimethylpropyl methyl 2,6-dimethyl-4-(m-nitrophenyl)-1,4-dihydropyridine-3,5-dicarboxylate

*3-(4-Formyl-1-homopiperazinyl)-2,2-dimethylpropyl methyl 2,6-dimethyl-4-(m-nitrophenyl)-1,4-dihydropyridine-3,5-dicarboxylate

*2,2-Dimethyl-3-[4-(2-methyl-2-propenyl)-1-piperazinyl]propyl Methyl 1,4-Dihydro-2,6-dimethyl-4-(3-nitrophenyl)-3,5-pyridinedicarboxylate Dihydrochloride

*2,2-Dimethyl-3-[4-(2-butenyl)-1-piperazinyl]propyl Methyl 1,4-Dihydro-2,6-dimethyl-4-(3-nitrophenyl)-3,5-pyridinedicarboxylate Dihydrochloride

*2,2-Dimethyl-3-(4-cinnamyl-1-piperazinyl)propyl Methyl 1,4-Dihydro-2,6-dimethyl-4-(3-nitrophenyl)-3,5-pyridinedicarboxylate Dihydrochloride

*2,2-Dimethyl-3-[4-(2-butynyl)-1-piperazinyl]propyl Methyl 1,4-Dihydro-2,6-dimethyl-4-(3-nitrophenyl)-3,5-pyridinedicarboxylate Dihydrochloride

*2,2-Dimethyl-3-[4-(4-pentynyl)-1-piperazinyl]propyl Methyl 1,4-Dihydro-2,6-dimethyl-4-(3-nitrophenyl)-3,5-pyridinedicarboxylate Dihydrochloride

*2,2-Dimethyl-3-(4-piperidinoethyl-1-piperazinyl)propyl Methyl 1,4-Dihydro-2,6-dimethyl-4-(3-nitrophenyl)-3,5-pyridinedicarboxylate Trihydrochloride

*2,2-Dimethyl-3-[4-(2-hydroxyethyl)-1-piperazinyl]-propyl Methyl 1,4-Dihydro-2,6-dimethyl-4-(3-nitrophenyl)-3,5-pyridinedicarboxylate Dihydrochloride

*2,2-Dimethyl-3-(4-benzoyl-1-piperazinyl)propyl Methyl 1,4-Dihydro-2,6-dimethyl-4-(3-nitrophenyl)-3,5-pyridinedicarboxylate Hydrochloride

*2,2-Dimethyl-3-[4-(1-methyl-2-oxopropyl)-1-piperazinyl]propyl Methyl 1,4-Dihydro-2,6-dimethyl-4-(3-nitrophenyl)-3,5-pyridinedicarboxylate Dihydrochloride

*2,2-Dimethyl-3-[4-(2-cyanoethyl)-1-piperazinyl]propyl Methyl 1,4-Dihydro-2,6-dimethyl-4-(3-nitrophenyl)-3,5-pyridinedicarboxylate Dihydrochloride

*2,2-Dimethyl-3-[4-(2-furoyl)-1-piperazinyl]propyl Methyl 1,4-Dihydro-2,6-dimethyl-4-(3-nitrophenyl)-3,5-pyridinedicarboxylate Hydrochloride The 1,4-dihydropyridine derivative (I) of the present invention can be, for example, produced as follows:

Method 1

The method in which the compound (II) represented by the general formula:

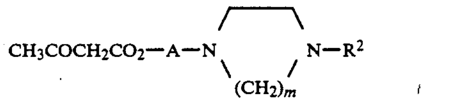

(II)

wherein m, $R^2$ and A have the same definitions as above, the compound (III) represented by the general formula:

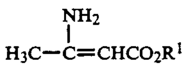

(III)

wherein $R^1$ has the same definition as above, and the compound (IV) represented by the general formula:

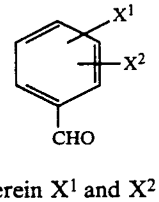

(IV)

wherein $X^1$ and $X^2$ have the same definitions as above, are reacted together.

Said reaction goes on preferably in the presence of an appropriate solvent. Any solvent can be used, as long as it does not interfere with this reaction; solvents which can be used include alkanols such as methanol, ethanol, propanol, isopropanol, butanol and sec-butanol; ethers such as ethyl ether, dioxane, tetrahydrofuran, ethylene glycol monomethyl ether and ethylene glycol dimethyl ether; acetic acid, pyridine, N-N-dimethylformamide, dimethyl sulfoxide, acetonitrile and a mixed solvent thereof.

Reaction temperature is normally about 10° to 150° C., preferably about 40° to 120° C. In particular, it is preferable that the reaction be carried out at a temperature near to the boiling point of the solvent used. Reaction time is normally 0.5 to 1.5 hours until the completion of the reaction. It is preferable that the compounds (II), (III) and (IV) be used in such amounts that any two of the three compounds are independently present in a ratio of 1 to 1.5 moles thereof to 1 mole of the remaining one compound.

Each starting compound is already known, or can be produced in accordance with a known method [see, for example, J. Am. Chem. Soc., 67, 1017 (1945)].

The compound (II) can be produced, for example, by the method indicated by the following equations:

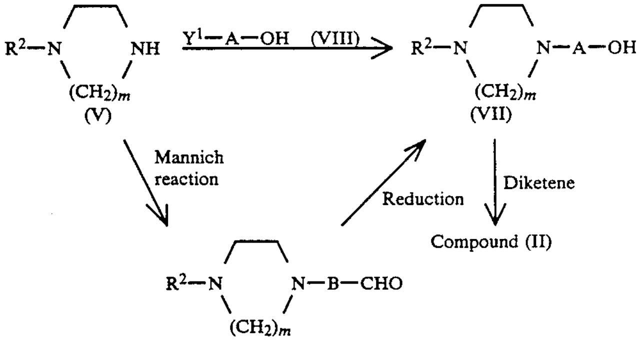

(VI)

wherein $Y^1$ represents a group which is reactive with amino group; B represents an alkylene comprising a carbon atom to which 2 alkyls are bonded and having in total at least 4 carbon atoms; the other symbols have the same definitions as above.

The group reactive with amino group herein represented by $Y^1$ is exemplified by halogen, p-toluenesulfonate, methanesulfonate, etc., and as preferable halogens, there may be mentioned, for example, a chlorine atom, a bromine atom, and an iodine atom.

The reaction between the compound (V) and the compound (VIII) is preferably carried out in the presence of a base such as sodium hydroxide, calcium hydroxide, sodium carbonate, potassium carbonate, pyridine, or triethylamine, and the reaction can be carried out at 20° to 150° C. by properly using solvents which do not adversely affect the reaction, for example, organic solvents such as toluene, benzene, methanol, ethanol, dioxane, tetrahydrofuran, acetone, methyl ethyl ketone and N,N-dimethylformamide; and water. In cases where the halogen represented by $Y^1$ in the formula (VIII) is a chlorine atom or bromine atom, sodium iodide, potassium iodide, etc. may be present in a ratio of about 0.1 to 2 moles thereof to 1 mole of the compound (V) for promoting the reaction.

The synthesis of the compound (VI) from the compound (V) is carried out by conventional Mannich reaction at 0° to 100° C. normally in an appropriate solvent (e.g. methanol, ethanol, isopropanol, acetic acid) using formalin and the corresponding aldehyde as a starting material. The compound (VI) is reduced by a reducing agent such as lithium aluminum hydride or sodium borohydride normally in an appropriate solvent (e.g. methanol, ethanol, isopropanol, ether, tetrahydrofuran) to form the compound (VII). The reaction is normally carried out in the temperature range of from 0° C. to the boiling point of the solvent used, and will almost complete itself within 24 hours, though reaction time varies according to the method of reduction.

Then, diketene is reacted with the compound (VII) to thereby produce the compound (II). This reaction is normally carried out at a reaction temperature of $-10°$ to 130° C., and may be conducted in the presence of a solvent which is inert to the reaction (e.g. methylene chloride, dioxane, tetrahydrofuran, benzene). In addition, for promoting the reaction, a basic catalyst (e.g. pyridine, triethylamine, 4-dimethylaminopyridine) may be used.

Method 2

The method in which the compound (IX) represented by the general formula:

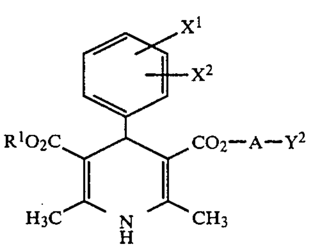

(IX)

wherein $Y^2$ represents a group which is reactive with amino group; $R^1$, $X^1$, $X^2$ and A have the same definitions as above, and the compound (V) represented by the general formula:

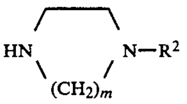

(V)

wherein m and $R^2$ have the same definitions as above, are reacted together.

The group reactive with amino group represented by $Y^2$ in the general formula (IX) is exemplified by the same groups as those mentioned above in relation to $Y^1$.

The reaction conditions for this reaction are in accordance with the above-mentioned method 1.

Method 3

The method in which the compound (X) represented by the general formula:

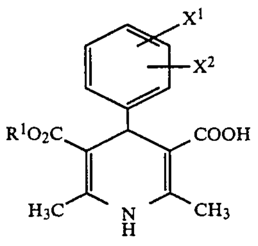

(X)

wherein $R^1$, $X^1$ and $X^2$ have the same definitions as above, or its reactive derivatives, and the compound (VII) represented by the general formula:

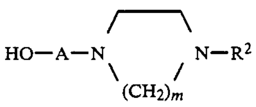

(VII)

wherein m, A and $R^2$ have the same definitions as above, are reacted together.

The reactive derivatives of the compound (X) are exemplified by acid halides (e.g. acid chloride, acid bromide) and active esters (e.g. tosylate).

Said reaction is an esterification reaction by carboxylic acid and alcohol, and is carried out by a per se known means.

Method 4

The method in which the compound (XI) represented by the general formula:

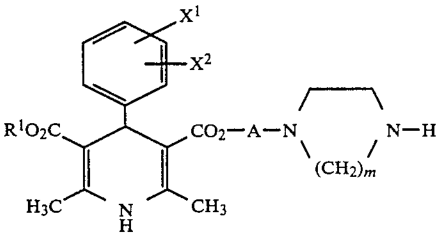

(XI)

wherein m, $R^1$, $X^1$, $X^2$, and A have the same definitions as above, and a compound of the general formula:

$R^2—Y^4$ (XII)

wherein $R^2$ has the same definition as above; $Y^4$ represents halogen, tosylate, or the like, are reacted together.

This reaction is preferably carried out in the presence of a base such as sodium hydroxide, calcium hydroxide, sodium carbonate, potassium carbonate, sodium acetate, potassium acetate, pyridine or triethylamine, and can be carried out at $-10°$ to 130° C. by properly using solvents which do not adversely affect the reaction, for example, organic solvents such as toluene, benzene, methanol, ethanol, dioxane, tetrahydrofuran, acetone, chloroform, dichloromethane, methyl ethyl ketone and N,N-dimethylformamide; and water. In cases where the halogen represented by $Y^4$ in the formula (XII) is a chlorine atom or bromine atom, sodium iodide, potassium iodide, etc. may be present in a ratio of about 0.1 to 2 moles thereof to 1 mole of the compound (XI) for promoting the reaction. The compound (XI) can be produced by the above-mentioned method, or can be obtained by deprotection from the compound (I) protected by a per se known protective group for amino group (e.g. $R^2$=formyl, tert-butoxycarbonyl, methoxycarbonyl, dichloroacetyl, trityl, etc.).

The 1,4-dihydropyridine derivative (I) thus obtained can be collected at any purity by means of per se known methods of separation and purification, for example, concentration, extraction, chromatography, reprecipitation and recrystallization.

Acid addition salt of the 1,4-dihydropyridine derivative (I) can be produced by a per se known method, and said acid addition salts can be converted to the 1,4-dihydropyridine derivative (I) in free form by a per se known method.

The 1,4-dihydropyridine derivative (I) of the present invention and acid addition salts thereof exhibit calcium antagonistic activities, such as smooth muscle relaxant activities, e.g. potent and long lasting hypotensive activity, coronary vasodilatation, cerebral vasodilatation, peripheral vasodilatation, bronchodilator activity, intraocular smooth muscle relaxant activity and renal vasodilatation; platelet aggregation inhibitory activity; antiallergic activity and anti-cancer activity, and, in addition, are of low toxicity.

Therefore, the 1,4-dihydropyridine derivative (I) and acid addition salts thereof are usable for therapeutic and preventive drugs for circulatory diseases such as hypertension, ischemic heart diseases (angina pectoris, myocardiac infarction, etc.), cerebral and peripheral circulatory disorders (cerebral infarction, transient ischemic attack, renal artery stenosis, etc.), in mammals such as humans, bovines, horses, dogs, mice and rats, and for therapeutic and preventive drugs for allergy (asthma), cataract, glaucoma, etc.

Namely, 1,4-dihydropyridine derivative of the present invention is a calcium antagonistic agent and useful as antihypertensive agent, antianginal agent, cerebral circulation improving agent, peripheral circulation improving agent, renal function improving agent, antiarteriosclerosis drug, smooth muscle relaxant, antiallergic drug, therapeutic drug for cataract and therapeutic drug for glaucoma.

Moreover, the 1,4-dihydropyridine derivative (I) and acid addition salts thereof are for the most part high in water solubility, and thus they are easy to formulate to, for example, eye drops, nasal drops, inhalations, injections, and liniments.

When used as pharmaceutical drugs, for example, the 1,4-dihydropyridine derivative (I) and acid addition salts thereof can be orally or parenterally administered. The form of administration is exemplified by oral drugs such as tablets, capsules and medicated syrups, and by parenteral drugs, for example, liquid injections in solution, emulsion, suspension, etc., and external preparations such as ointments, creams, suppositories, poultices, eye drops, nasal drops, inhalations, liniments and aerosols.

The pharmaceutical preparations in the above-mentioned administration forms can be produced by preparation by a routine method in the presence of additives which are necessary for preparing said preparations, such as conventional carriers, excipients, binders and stabilizers.

Dose and administration frequency can vary according to symptoms, age, body weight, and administration form, but any of the 1,4-dihydropyridine derivative (I) and acid addition salts thereof, when used as a hypotensive drug, for example, can be normally administered to an adult in a dose of about 0.1 to 100 mg, preferably 0.5 to 50 mg a day in single or several administrations.

The results of pharmacological tests showing the effectiveness of the 1,4-dihydropyridine derivative (I) are hereinafter presented. Experimental example 1. Hypotensive activity [Method] Male spontaneously hypertensive rats at the 12th to 16th week in age and presenting a systolic pressure of around 200 mmHg were used as experimental animals, and 3 to 8 animals were assigned to each group. The subject compound (indicated by the example number), in an aqueous solution or 5% gum arabic suspension, was orally administered in a dose of 10 mg/kg. At the 4th and 8th hours following the administration, the systolic pressure at tail vein of each rat was noninvasively measured by means of a sphygmomanometer (USM-105, Ueda Seisakusho, Japan). A group of rats administered the solvent alone was used as a control group. [Results] The hypotensive activities (preadministration blood pressure-postadministration blood pressure) of the 1,4-dihydropyridine derivative (I) and acid addition salts thereof are shown in Table 1.

As shown in Table 1, the 1,4-dihydropyridine derivative (I) and acid addition salts thereof were more potent and more long lasting in hypotensive activity in comparison with a known dihydropyridine derivative (nicardipine).

TABLE 1

| | Hypotensive Activities | |
|---|---|---|
| | Change in blood pressure (mmHg) | |
| Example Number | 4 hours after administration | 8 hours after administration |
| Control group | −2 | +1 |
| 2 | −81 | −104 |
| 5 | −90 | −87 |
| 6 | −64 | −88 |
| 7 | −76 | −84 |
| 8 | −56 | −90 |
| 12 | −70 | −102 |
| 13 | −69 | −77 |
| 14 | −43 | −88 |
| 15 | −52 | −47 |
| 16 | −34 | −52 |
| 17 | −112 | −107 |
| 19 | −86 | −85 |
| 20 | −84 | −82 |
| 21 | −112 | −98 |
| 23 | −104 | −82 |
| 24 | −91 | −69 |
| 26 | −53 | −32 |
| 27 | −83 | −60 |
| Nicardipine | −29 | −22 |

Gum arabic or water was administered to rats of the control group.

Experimental example 2

Water solubility test

Method

The subject compounds (indicated by the example number), after being powdered, were placed in water and vigorously shaken at 20°±5° C. for 30 seconds a 5-minute intervals, and within 30 minutes, the amount of water required to dissolve 1 g of the compound (I) of the present invention therein was measured.

Results

The results showing the solubilities in water of the 1,4-dihydropyridine derivative (I) and acid addition salts thereof are presented in Table 2.

TABLE 2

| | Solubilities in Water |
|---|---|
| Example number | Amount (ml) of water required to dissolve 1 g of the subject compounds |
| 2 | 2 |
| 12 | 2 |
| 14 | 2 |
| 15 | 2 |
| 16 | 2 |
| 17 | 3.2 |
| 19 | 2 |
| 20 | 1.6 |
| 21 | 2 |
| 23 | 2 |

TABLE 2-continued

| Solubilities in Water | |
|---|---|
| Example number | Amount (ml) of water required to dissolve 1 g of the subject compounds |
| 24 | 2 |
| 25 | 2 |
| 26 | 2 |
| 27 | 2 |
| Nicardipine | 160 |
| Nifedipine | >10000 |

EXAMPLE 1

Synthesis of 3-[4-(2-furoyl)-1-piperazinyl]-2,2-dimethylpropyl methyl 2,6-dimethyl-4-(m-nitrophenyl)-1,4-dihydropyridine-3,5-dicarboxylate hydrochloride 0.73 g of 3-(1-piperazinyl)-2,2-dimethylpropyl methyl 2,6-dimethyl-4-(m-nitrophenyl)-1,4-dihydropyridine-3,5-dicarboxylate dihydrochloride was dissolved in 5 ml of tetrahydrofuran, and 0.6 ml of triethylamine and 0.13 ml of 2-furoyl chloride were added; the mixture was then stirred for 10 minutes while cooling with ice. After evaporating the solvent, the residue was purified by the chromatography method [20 g silica gel, n-hexane:ethyl acetate (2:5)] to give 0.4 g of an oily substance. This oily substance was dissolved in diethyl ether; a slightly excessive amount of a solution of hydrogen chloride in ethanol was added; the solid which separated was collected by filtration to give 0.42 g of the subject compound (yield: 52%). The IR and NMR data of the compound thus obtained are as follows:

IR (Nujol, $cm^{-1}$) 3300, 1695, 1620, 1525
$^1H$—NMR (DMSO-$d_6$, δ value)
1.05 (6H, s, $>C(CH_3)_2$)
2.26 (3H, s, $=\overset{|}{C}-CH_3$)
2.35 (3H, s, $=\overset{|}{C}-CH_3$)
3.57 (3H, s, $-CO_2CH_3$)
3.95 (2H, s, $-CO_2CH_2-$)
5.00 (1H, s, $C_4$—H)
6.60 (1H, dd, J=4Hz, 4Hz, 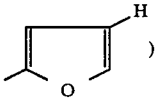 )
7.05 (1H, d, J=4Hz, 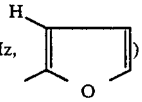 )
7.4~8.1 (5H, m, phenyl, 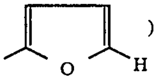 )
9.07 (1H, br, >NH)

EXAMPLE 2

Synthesis of 3-(4-allyl-1-piperazinyl)-2,2-dimethylpropyl methyl 2,6-dimethyl-4-(m-nitrophenyl)-1,4-dihydropyridine-3,5-dicarboxylate dihydrochloride 1.5 g of 3-(1-piperazinyl)-2,2-dimethylpropyl methyl 2,6-dimethyl-4-(m-nitrophenyl)-1,4-dihydropyridine-3,5-dicarboxylate dihydrochloride was dissolved in 10 ml of tetrahydrofuran, and 1.2 ml of triethylamine and 0.22 ml of allyl chloride were added. The mixture was then stirred at 50° C. for 12 hours. After evaporating the solvent, the residue was purified by the chromatography method [20 g silica gel, eluted with ethyl acetate] to give 1.1 g of an oily substance. This oily substance was dissolved in diethyl ether; a slightly excessive amount of a solution of hydrogen chloride in ethanol was added; the solid which separated was collected by filtration, after which it was recrystallized from ethanol to thereby give 1.1 g of the subject compound (yield: 75%). The IR and NMR data of the compound thus obtained are as follows:

IR (Nujol, $cm^{-1}$) 3340, 1690, 1520
$^1H$—NMR (DMSO-$d_6$, δ value)
0.96 (6H, s, $>C(CH_3)_2$)
2.27 (3H, s, $=\overset{|}{C}-CH_3$)
2.37 (3H, s, $=\overset{|}{C}-CH_3$)
3.60 (3H, s, $-CO_2CH_3$)
3.90 (2H, s, $-CO_2CH_2-$)
5.00 (1H, s, $C_4$—H)
5.3~6.0 (3H, m, $-CH=CH_2$)
7.4~8.2 (4H, m, phenyl)
9.20 (1H, br, >NH)

EXAMPLE 3

Synthesis of 3-[4-(tert-butyloxycarbonyl)-1-piperazinyl]-2,2-dimethylpropyl methyl 2,6-dimethyl-4-(m-nitrophenyl)-1,4-dihydropyridine-3,5-dicarboxylate 1.6 g of m-nitrobenzaldehyde, 3.7 g of 3-[4-(tert-butyloxycarbonyl)-1-piperazinyl]-2,2-dimethylpropyl acetoacetate, and 1.3 g of methyl 3-aminocrotonate were dissolved in 10 ml of isopropanol, and the solution was subjected to heating reflux for 12 hours. Then, the solvent was concentrated under reduced pressure. Diethyl ether was added to the residue to give 2.7 g of a colorless powdery crystal (yield: 44%). The IR and NMR data of the compound thus obtained are as follows:

IR (Nujol, $cm^{-1}$) 3300, 1700~1640, 1520
$^1H$—NMR ($CDCl_3$, δ value)
0.85 (3H, s, $>\overset{|}{C}-CH_3$)
0.89 (3H, s, $>\overset{|}{C}-CH_3$)
1.45 (9H, s, $-C(CH_3)_3$)

-continued 2.07 (2H, s, $—CH_2N<$)

2.30 (4H, br-t, 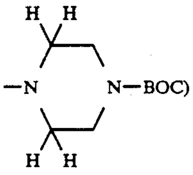)

2.32 (3H, s, $=C—CH_3$)

2.40 (3H, s, $=C—CH_3$)

3.30 (4H, br-t, 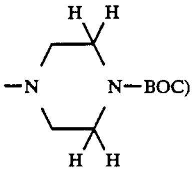)

3.67 (3H, s, $—CO_2CH_3$)
3.82 (2H, s, $—CO_2CH_2—$)
5.41 (1H, s, $C_4—H$)
6.25 (1H, br, >NH)
7.4~8.5 (4H, m, phenyl)

EXAMPLE 4

Synthesis of 3-(4-formyl-1-piperazinyl)-2,2-dimethylpropyl methyl 2,6-dimethyl-4-(m-nitrophenyl)-1,4-dihydropyridine-3,5-dicarboxylate 425 mg of m-nitrobenzaldehyde, 830 mg of 3-(4-formyl-1-piperazinyl)-2,2-dimethylpropyl acetoacetate, and 324 mg of methyl 3-aminocrotonate were dissolved in 6 ml of isopropanol, and the solution was subjected to heating reflux for 12 hours. Then, the solvent was concentrated under reduced pressure. The residue was purified by the chromatography method [30 g silica gel, eluted with ethyl acetate) to give 1090 mg of the subject compound (yield: 75%). The IR and NMR data of the compound thus obtained are as follows:

IR (Nujol, $cm^{-1}$) 3290, 1700~1650, 1525

$^1H—NMR$ ($CDCl_3$, δ value)
0.81, 0.85 (6H, s, $>C(CH_3)_2$)
2.10 (2H, s, $—CH_2N<$)

-continued 2.32, 2.40 (6H, s, $=C—CH_3$)

2.40 (4H, br, 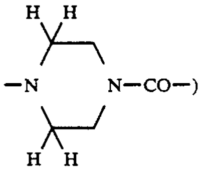)

3.40 (4H, br, 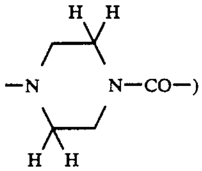)

3.69 (3H, s, $—CO_2CH_3$)
3.83 (2H, s, $—CO_2CH_2—$)
5.11 (1H, s, $C_4—H$)
6.20 (1H, br, >NH)
7.2~8.2 (4H, m, phenyl)
7.92 (1H, s, >N—CHO)

EXAMPLES 5 THROUGH 28

The compounds of the formula:

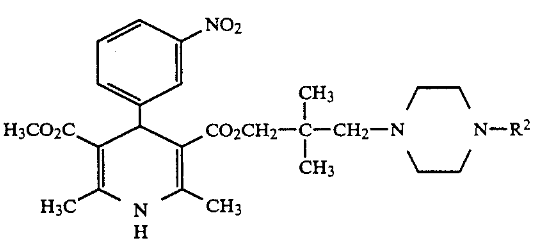

wherein $R^2$ is any of the groups listed in Table 3 were produced in accordance with the method of Example 1 or Example 2. In the table, —φ means a phenyl group. The IR and NMR data of the compounds thus obtained are as shown in Table 3.

EXAMPLES 29 AND 30

The compounds of the formula:

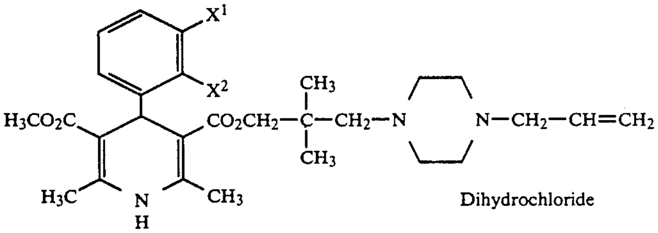

Dihydrochloride wherein $X^1$ and $X^2$ independently represent any of the groups listed in Table 4 were produced in accordance with the method of Example 3. The IR and NMR data of the compounds thus obtained are as shown in Table 4.

TABLE 3

| Example No. | $R^2$ | IR ($cm^{-1}$) (Nujol) | $^1$H-NMR (DMSO-$d_6$, δ value) | Method |
|---|---|---|---|---|
| 5 | $-COCH_2\phi$ hydrochloride | 3250<br>1690<br>1650<br>1525 | 1.00 (6H, s, $>C(CH_3)_2$) 2.28 (3H, s, $=C-CH_3$)<br>2.36 (3H, s, $=C-CH_3$) 3.59 (3H, s, $-CO_2CH_3$)<br>3.75 (2H, s, $-COCH_2\phi$) 3.92 (2H, s, $-CO_2CH_2-$)<br>5.00 (1H, s, $C_4-H$)<br>7.1~8.1 (9H, m, phenyl) 9.17 (1H, br, $>NH$) | 1 |
| 6 | $-CO\phi$ hydrochloride | 3200<br>1690<br>1640<br>1520 | 1.00 (6H, s, $>C(CH_3)_2$) 2.25 (3H, s, $=C-CH_3$)<br>2.35 (3H, s, $=C-CH_3$) 3.57 (3H, s, $-CO_2CH_3$)<br>3.95 (2H, s, $-CO_2CH_2-$) 5.00 (1H, s, $C_4-H$)<br>7.3~8.1 (9H, m, phenyl) 9.18 (1H, br, $>NH$) | 1 |
| 7 | $-COCH=CH\phi$ hydrochloride | 3200<br>1690<br>1650<br>1525 | 1.05 (6H, s, $>C(CH_3)_2$) 2.25 (3H, s, $=C-CH_3$)<br>2.35 (3H, s, $=C-CH_3$) 3.57 (3H, s, $-CO_2CH_3$)<br>3.95 (2H, s, $-CO_2CH_2-$) 5.00 (1H, s, $C_4-H$)<br>7.2~8.1 (11H, m, phenyl, $-CH=CH-$)<br>9.20 (1H, br, $>NH$) | 1 |
| 8 | $-COCH_3$ hydrochloride | 3250<br>1690<br>1620<br>1520 | 1.05 (6H, s, $>C(CH_3)_2$) 2.03 (3H, s, $-COCH_3$)<br>2.27 (3H, s, $=C-CH_3$) 2.37 (3H, s, $=C-CH_3$)<br>3.60 (3H, s, $-CO_2CH_3$) 3.95 (2H, s, $-CO_2CH_2-$)<br>5.00 (1H, s, $C_4-H$)<br>7.4~8.2 (4H, m, phenyl) 9.24 (1H, br, $>NH$) | 1 |
| 9 | $-COCH_2Cl$ hydrochloride | 3300<br>1690<br>1660<br>1520 | 1.00 (6H, s, $>C(CH_3)_2$) 2.25 (3H, s, $=C-CH_3$)<br>2.33 (3H, s, $=C-CH_3$) 2.57 (3H, s, $-CO_2CH_3$)<br>3.90 (2H, s, $-CO_2CH_2-$) 4.38 (2H, s, $-COCH_2Cl$)<br>5.00 (1H, s, $C_4-H$)<br>7.4~8.1 (4H, m, phenyl) 9.15 (1H, br, $>NH$) | 1 |
| 10 | $-COCH(CH_3)_2$ hydrochloride | 3200<br>1690<br>1650<br>1520 | 0.98 (12H, m, $>C(C\underline{H_3})_2$, $-COCH(C\underline{H_3})_2$)<br>2.28 (3H, s, $=C-CH_3$) 2.38 (3H, s, $=C-CH_3$)<br>3.60 (3H, s, $-CO_2CH_3$) 3.96 (2H, s, $-CO_2CH_2-$)<br>5.00 (1H, s, $C_4-H$)<br>7.4~8.1 (4H, m, phenyl) 9.23 (1H, br, $>NH$) | 1 |
| 11 | $-COCH_2N$ 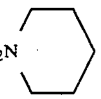 dihydrochloride | 3200<br>1660<br>1525 | 0.85 (6H, s, $>C(CH_3)_2$) 1.3~2.0 (6H, m, 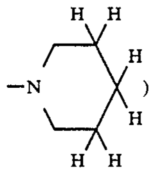)<br>2.27 (3H, s, $=C-CH_3$) 2.37 (3H, s, $=C-CH_3$)<br>3.60 (3H, s, $-CO_2CH_3$) 3.80 (2H, s, $-CO_2CH_2-$)<br>4.27 (2H, s, $-COCH_2N<$) 5.00 (1H, s, $C_4-H$)<br>7.4~8.1 (4H, m, phenyl) 9.35 (1H, br, $>NH$) | 1 |

TABLE 3-continued

| Example No. | $R^2$ | IR ($cm^{-1}$) (Nujol) | $^1$H-NMR ($DMSO-d_6$, δ value) | Method |
|---|---|---|---|---|
| 12 | $-CH_2-C{\equiv}CH$ dihydro-chloride | 3300<br>1680<br>1520 | 0.97 (6H, s, >C($CH_3$)$_2$) 2.27 (3H, s, =C—$CH_3$)<br>2.38 (3H, s, =C—$CH_3$) 3.59 (3H, s, —$CO_2CH_3$)<br>3.90 (2H, s, —$CO_2CH_2$—) 5.00 (1H, s, $C_4$—H)<br>7.5~8.1 (4H, m, phenyl) 9.23 (1H, br, >NH) | 2 |
| 13 | $-CH_2CH{=}CH\phi$ dihydro-chloride | 3400<br>1685<br>1520 | 0.92 (6H, s, >C($CH_3$)$_2$) 2.26 (3H, s, =C—$CH_3$)<br>2.35 (3H, s, =C—$CH_3$) 3.59 (3H, s, —$CO_2CH_3$)<br>3.85 (2H, s, —$CO_2CH_2$—) 5.00 (1H, s, $C_4$—H)<br>7.2~8.1 (11H, m, phenyl), —CH=CH)<br>9.16 (1H, br, >NH) | 2 |
| 14 | $-CH_2CH_2CN$ dihydro-chloride | 3350<br>1690<br>1525 | 0.94 (6H, s, >C($CH_3$)$_2$) 2.25 (3H, s, =C—$CH_3$)<br>2.35 (3H, s, =C—$CH_3$) 3.58 (3H, s, —$CO_2CH_3$)<br>3.86 (2H, s, —$CO_2CH_2$—) 5.00 (1H, s, $C_4$—H)<br>7.4~8.1 (4H, m, phenyl) 9.18 (1H, br, >NH) | 2 |
| 15 | $-CH_2CH_2OH$ dihydro-chloride | 3300<br>1690<br>1520 | 0.94 (6H, s, >C($CH_3$)$_2$) 2.25 (3H, s, =C—$CH_3$)<br>2.35 (3H, s, =C—$CH_3$) 3.59 (3H, s, —$CO_2CH_3$)<br>3.86 (2H, s, —$CO_2CH_2$—) 5.00 (1H, s, $C_4$—H)<br>7.4~8.1 (4H, m, phenyl) 9.16 (1H, br, >NH) | 2 |
| 16 | $-CH_2CH_2N$ 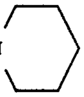<br>trihydro-chloride | 3350<br>1690<br>1525 | 0.97 (6H, s, >C($CH_3$)$_2$) 1.3~2.0 (6H, m, —N 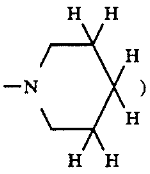 )<br>2.25 (3H, s, =C—$CH_3$) 2.35 (3H, s, =C—$CH_3$)<br>3.58 (3H, s, —$CO_2CH_3$) 3.87 (2H, s, —$CO_2CH_2$—)<br>5.00 (1H, s, $C_4$—H)<br>7.4~8.1 (4H, m, phenyl) 9.20 (1H, br, >NH) | 2 |
| 17 | $CH_3$<br>$-CH_2C{=}CH_2$<br>dihydro-chloride | 3400<br>1690<br>1525 | 1.00 (6H, s, >C($CH_3$)$_2$) 1.92 (3H, s, —C($CH_3$)=$CH_2$)<br>2.28 (3H, s, =C—$CH_3$) 2.39 (3H, s, =C—$CH_3$)<br>3.60 (3H, s, —$CO_2CH_3$) 3.92 (2H, s, —$CO_2CH_2$—)<br>5.00 (1H, s, $C_4$—H) 5.26 (2H, s, =$CH_2$)<br>7.4~8.1 (4H, m, phenyl) 9.25 (1H, br, >NH) | 2 |
| 18 | $-CH_2CO\phi$ dihydro-chloride | 3300<br>1690<br>1520 | 0.96 (6H, s, >C($CH_3$)$_2$) 2.26 (3H, s, =C—$CH_3$)<br>2.37 (3H, s, =C—$CH_3$) 3.60 (3H, s, —$CO_2CH_3$)<br>3.90 (2H, s, —$CO_2CH_2$—)<br>5.00 (3H, br, $C_4$—H), >$NCH_2CO$—)<br>7.4~8.2 (9H, m, phenyl) 9.23 (1H, br, >NH) | 2 |

TABLE 3-continued

| Example No. | $R^2$ | IR ($cm^{-1}$) (Nujol) | $^1$H-NMR ($DMSO-d_6$, δ value) | Method |
|---|---|---|---|---|
| 19 | $-CHCOCH_3$ with $CH_3$ on the CH<br>dihydro-<br>chloride | 3300<br>1690<br>1520 | 0.95 (6H, s, $>C(CH_3)_2$)<br>1.42 (3H, d, J=6Hz, $-CH(CH_3)CO-$)<br>2.25 (6H, s, $=C-CH_3$, $-COCH_3$)<br>2.35 (3H, s, $=C-CH_3$) 3.60 (3H, s, $-CO_2CH_3$)<br>3.90 (2H, s, $-CO_2CH_2-$) 5.00 (1H, br, $C_4-H$)<br>7.4~8.1 (4H, m, phenyl) 9.20 (1H, br, $>NH$) | 2 |
| 20 | $-CH_2CH=CHCH_3$<br>dihydro-<br>chloride | 3350<br>1690<br>1520 | 0.94 (6H, s, $>C(CH_3)_2$)<br>1.75 (3H, d, J=6Hz, $=C-CH_3$)<br>2.26 (3H, s, $=C-CH_3$) 2.36 (3H, s, $=C-CH_3$)<br>3.60 (3H, s, $-CO_2CH_3$) 3.87 (2H, s, $-CO_2CH_2-$)<br>5.00 (1H, s, $C_4-H$)<br>7.4~8.1 (4H, m, phenyl) 9.20 (1H, br, $>NH$) | 2 |
| 21 | $-(CH_2)_3C\equiv CH$<br>dihydro-<br>chloride | 3300<br>1680<br>1520 | 0.96 (6H, s, $>C(CH_3)_2$) 2.00 (1H, br, $-C\equiv CH$)<br>2.27 (3H, s, $=C-CH_3$) 2.37 (3H, s, $=C-CH_3$)<br>3.60 (3H, s, $-CO_2CH_3$) 3.88 (2H, s, $-CO_2CH_2-$)<br>5.00 (1H, s, $C_4-H$)<br>7.4~8.1 (4H, m, phenyl) 9.20 (1H, br, $>NH$) | 2 |
| 22 | 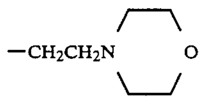<br>trihydro-<br>chloride | 3200<br>1690<br>1520 | 0.98 (6H, s, $>C(CH_3)_2$) 2.25 (3H, s, $=C-CH_3$)<br>2.35 (3H, s, $=C-CH_3$) 3.60 (3H, s, $-CO_2CH_3$)<br>5.00 (1H, s, $C_4-H$)<br>7.4~8.2 (4H, m, phenyl) 9.20 (1H, br, $>NH$) | 2 |
| 23 | $-CH_2CN$<br>dihydro-<br>chloride | 3200<br>1690<br>1520 | 0.98 (6H, s, $>C(CH_3)_2$) 2.25 (3H, s, $=C-CH_3$)<br>2.37 (3H, s, $=C-CH_3$) 3.58 (3H, s, $-CO_2CH_3$)<br>3.80 (2H, s, $-CH_2CN$) 3.91 (2H, s, $-CO_2CH_2-$)<br>5.00 (1H, s, $C_4-H$)<br>7.4~8.1 (4H, m, phenyl) 9.25 (1H, br, $>NH$) | 2 |
| 24 | $-CH_2CN_2ONO_2$<br>dihydro-<br>chloride | 3400<br>1690<br>1640<br>1520 | 0.99 (6H, s, $>C(CH_3)_2$) 2.27 (3H, s, $=C-CH_3$)<br>2.36 (3H, s, $=C-CH_3$) 3.60 (3H, s, $-CO_2CH_3$)<br>3.90 (2H, s, $-CO_2CH_2-$)<br>4.7~5.0 (3H, m, $C_4-H$, $-CH_2ONO_2$)<br>7.4~8.1 (4H, m, phenyl) 9.20 (1H, br, $>NH$) | 2 |

TABLE 3-continued

| Example No. | $R^2$ | IR ($cm^{-1}$) (Nujol) | $^1$H-NMR (DMSO-$d_6$, δ value) | Method |
|---|---|---|---|---|
| 25 | $-CH_2CO_2C_2H_5$ dihydro-chloride | 3300<br>1690<br>1520 | 1.05 (6H, s, $>C(CH_3)_2$)<br>1.26 (3H, t, J=7Hz, $-CH_2\underline{CH_3}$)<br>2.40 (3H, s, $=C-CH_3$) 3.01 (2H, s, $>NCH_2C-$)<br>3.60 (3H, s, $-CO_2CH_3$) 3.95 (2H, s, $-CO_2CH_2-$)<br>4.20 (2H, s, $>NCH_2C-$) 5.00 (1H, s, $C_4$—H)<br>7.4~8.1 (4H, m, phenyl) 9.34 (1H, br, $>NH$) | 2 |
| 26 | $-CH_2CON$ 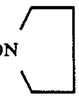<br>dihydro-chloride | 3380<br>1680<br>1650<br>1525 | 1.17 (6H, s, $>C(CH_3)_2$) 1.6~2.2 (4H, m, $-N$ 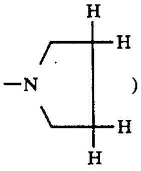 )<br>2.30 (3H, s, $=C-CH_3$) 2.40 (3H, s, $=C-CH_3$)<br>2.95 (2H, br, $>NCH_2C-$) 3.61 (3H, s, $-CO_2CH_3$)<br>3.99 (2H, s, $-CO_2CH_2-$) 4.39 (2H, s, $>NCH_2C-$)<br>5.02 (1H, s, $C_4$—H)<br>7.4~8.1 (4H, m, phenyl) 9.10 (1H, br, $>NH$) | 2 |
| 27 | $-CH_2CONHCH_3$ dihydro-chloride | 3400<br>1680<br>1520 | 1.10 (6H, s, $>C(CH_3)_2$) 2.32 (3H, s, $=C-CH_3$)<br>2.41 (3H, s, $=C-CH_3$) 2.77 (3H, d, J=5Hz, $-NH\underline{CH_3}$)<br>2.92 (2H, s, $>NCH_2C-$) 3.67 (3H, s, $-CO_2CH_3$)<br>4.05 (4H, s, $-CO_2CH_2-$, $>NCH_2C-$)<br>5.05 (1H, s, $C_4$—H) 7.2~8.2 (4H, m, phenyl)<br>8.5~8.8 (1H, m, $-N\underline{H}CH_3$) | 2 |
| 28 | $-CH_2CH_2F$ dihydro-chloride | 3340<br>1680<br>1520 | 0.93 (6H, s, $>C(CH_3)_2$) 2.28 (3H, s, $=C-CH_3$)<br>2.38 (3H, s, $=C-CH_3$) 3.60 (3H, s, $-CO_2CH_3$)<br>3.88 (2H, s, $-CO_2CH_2-$) 5.01 (1H, s, $C_4$—H)<br>4.50, 5.30 (2H, m, $>NCH_2\underline{CH_2}CH_2F$)<br>7.46~8.20 (4H, m, phenyl) 9.20 (1H, br, $>NH$) | 2 |

TABLE 4

| Example No. | $X^1$ | $X^2$ | IR ($cm^{-1}$) (Nujol) | $^1$H-NMR (DMSO-$d_6$, Value) |
|---|---|---|---|---|
| 29 | Cl | H | 3400<br>1690<br>1525 | 0.98 (6H, s, $>C(CH_3)_2$) 2.28 (3H, s, $=C-CH_3$)<br>2.38 (3H, s, $=C-CH_3$) 3.60 (3H, s, $-CO_2CH_3$)<br>3.89 (2H, s, $-CO_2CH_2-$) 5.00 1H, s, $C_4$—H)<br>5.3~6.0 (3H, m, $-CH=CH_2$)<br>7.0~8.5 (4H, m, phenyl) 9.16 (1H, br, $>NH$) |

TABLE 4-continued

| Example No. | $X^1$ | $X^2$ | IR ($cm^{-1}$) (Nujol) | $^1$H-NMR (DMSO-$d_6$, Value) |
|---|---|---|---|---|
| 30 | Cl | Cl | 3400 1690 1525 | 0.97 (6H, s, >$C(CH_3)_2$) 2.27 (3H, s, =C—$CH_3$) 2.37 (3H, s, =C—$CH_3$) 3.58 (3H, s, —$CO_2CH_3$) 3.89 (2H, s, —$CO_2CH_2$—) 5.00 (1H, s, $C_4$—H) 5.3~6.0 (3H, m, —CH=$CH_2$) 6.8~7.5 (3H, m, phenyl 9.20 (1H, br, >NH) |

FORMULATION EXAMPLES OF PHARMACEUTICAL PREPARATIONS

EXAMPLE 1

| Formulation example for nasal drops: | |
|---|---|
| Compound of this invention | 0.1 mg |
| Physiological saline solution | |
| Total | 100.0 ml |

EXAMPLE 2

| Formulation example for eye drops: | |
|---|---|
| Compound of this invention | 0.1 mg |
| Sterile solution for eye-drops (pH 5.0) | |
| Total | 100.0 ml |

EXAMPLE 3

| Formulation example for injection (aqueous solution): (in 2 ml ampule) | |
|---|---|
| Compound of this invention | 1 mg |
| Distilled water for injection | |
| Total | 2 ml |

EXAMPLE 4

| Formulation example for injection (solid injection): (in each vial) | |
|---|---|
| Compound of this invention | 1 mg |
| Mannitol | 100 mg |

EXAMPLE 5

| Formulation example for tablets | |
|---|---|
| Compound of this invention | 10 mg |
| Lactose | 80 mg |
| Magnesium stearate | 2 mg |
| Talc | 4 mg |

According to the above composition, an aqueous solution of starch was added to a premixture of the compound of this invention and lactose, and this was followed by kneading. Then, the resulting mixture was dried and pulverized to thereby give a powder of uniform particles. To this powder a mixture of talc and magnesium stearate was added, and the resulting mixture was tableted to thereby produce the desired tablets.

EXAMPLE 6

| Formulation example for capsules | |
|---|---|
| Compound of this invention | 5 mg |
| Lactose | 100 mg |
| Polyvinylpyrrolidone | 3 mg |

According to the above composition, polyvinylpyrrolidone and an alcohol solution of stearic acid were added to a premixture of the compound of this invention and lactose, and this was followed by kneading. Then, the resulting mixture was grandulated to thereby give granules. The resulting granules, after drying, were filled in No. 4 capsular containers to thereby produce the desired capsules.

REFRENCE EXAMPLE 1

Synthesis of 3-[4-(tert-butyloxycarbonyl)-1-piperazinyl]-2,2-dimethylpropanol

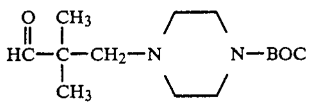

2.9 g of N-(tert-butyloxycarbonyl)piperazine and 1.6 ml of 35% formalin were dissolved in 8 ml of acetic acid, and the resulting solution was stirred at room temperature for 30 minutes. Then, 1.5 ml of isobutylaldehyde was added, and the resulting mixture was stirred at 50° C. for 12 hours. After concentration under reduced pressure, the residue was extracted with ethyl acetate and washed with saturated aqueous sodium bicarbonate. After drying with anhydrous sodium sulfate, the solvent was evaporated under reduced pressure to give 3.9 g of a colorless powdery crystal (yield: 94%). The IR and NMR data of the compound thus obtained are as follows:

IR (Nujol, $cm^{-1}$) 1720, 1700
$^1$H—NMR ($CDCl_3$, δ value)
1.06 (6H, s, >$C(CH_3)_2$)
1.44 (9H, s, —$C(CH_3)_3$)

2.36 (4H, t, J=5Hz, 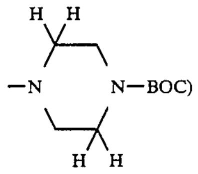)

2.48 (2H, s, —$CH_2$N<)

-continued 3.34 (4H, t, J=5Hz, 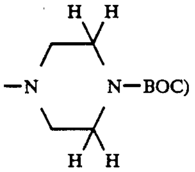

9.50 (1H, s, —CHO)

REFERENCE EXAMPLE 2

Synthesis of 3-(4-formyl-1-piperazinyl)-2,2-dimethylpropanal

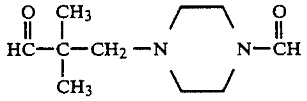

Formylpiperazine as the starting material was treated in the same manner as in Reference example 1 to give the subject compound (yield: 98%). The IR and NMR data of the compound thus obtained are as follows:

IR (Neat, $cm^{-1}$) 1715, 1670

$^1H$—NMR($CDCl_3$, δ value)

1.09 (6H, s, $>C(CH_3)_2$)

2.50 (2H, s, $-CH_2N\langle$)

2.45 (4H, m, 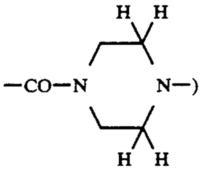

3.40 (4H, m, 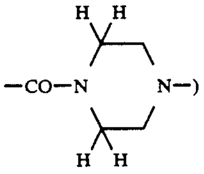

7.95 (1H, br-s, >N—CHO)

9.50 (1H, s, 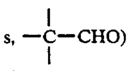

REFERENCE EXAMPLE 3

Synthesis of 3-[4-(tert-butyloxycarbonyl)-1-piperazinyl]-2,2-dimethylpropanol

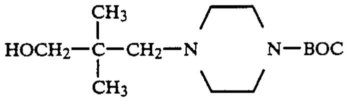

0.14 g of sodium borohydride was dissolved in 4 ml of isopropanol, and 3.8 g of 3-[4-(tert-butyloxycarbonyl)-1-piperazinyl]-2,2-dimethylpropanal was added. The solution was stirred at room temperature for 2 hours; then, water was added, and the solution was extracted with methylene chloride. After drying with anhydrous sodium sulfate, the solvent was evaporated under reduced pressure to give 3.8 g of a needle-like crystal (yield: 99%). The IR and NMR data of the compound thus obtained are as follows:

IR (Neat, $cm^{-1}$) 3450, 1700

$^1H$—NMR($CDCl_3$, δ value)

0.92 (6H, s, $>C(CH_3)_2$)

1.45 (9H, s, $-C(CH_3)_3$)

2.37 (2H, s, $-CH_2N\langle$)

2.54 (4H, br-t, 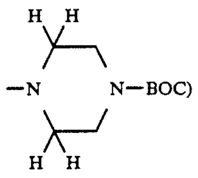

3.45 (4H, br-t, 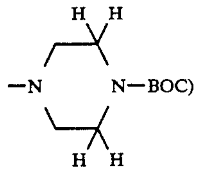

3.48 (2H, s, $-CH_2OH$)

4.35 (1H, br, —OH)

REFERENCE EXAMPLE 4

Synthesis of 3-(4-formyl-1-piperazinyl)-2,2-dimethylpropanol

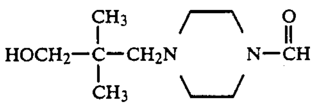

3-(4-Formyl-1-piperazinyl)-2,2-dimethylpropanal as the starting material was treated in the same manner as in Reference example 3 to give the subject compound (yield: 85%). The IR and NMR data of the compound thus obtained are as follows:

IR (Neat, $cm^{-1}$) 3450, 1670

$^1H$—NMR($CDCl_3$, δ value)

0.93 (6H, s, $>C(CH_3)_2$)

2.38 (2H, s, $-CH_2N<$)

2.60 (4H, m, —CO— 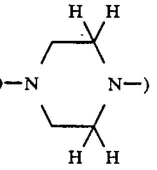 )

3.40 (4H, m, —CO— 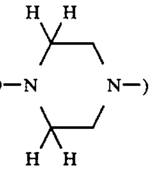 )

3.45 (2H, s, $-\underset{|}{\overset{|}{C}}CH_2OH$)

4.50 (1H, br, —OH)

REFERENCE EXAMPLE 5

Synthesis of 3-[4-(tert-butyloxycarbonyl)-1-piperazinyl]-2,2-dimethylpropyl acetoacetate

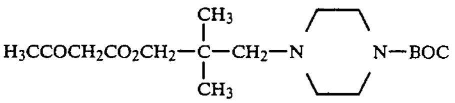

3.7 g of 3-[4-(tert-butyloxycarbonyl)-1-piperazinyl]-2,2-dimethylpropanol and 30 mg of 4-dimethylaminopyridine were dissolved in 10 ml of methylene chloride, and diketene was added while cooling the solution with ice. After stirring the solution for 30 minutes under cooling with ice, water was added and the solution was extracted with methylene chloride. The resulting extract was concentrated under reduced pressure to give 4.7 g of an oily product (yield: 97%). The IR and NMR data of the compound thus obtained are as follows:

IR (Neat, $cm^{-1}$) 1740, 1720, 1700

$^1H$—NMR($CDCl_3$, δ value)

0.90 (6H, s, $>C(CH_3)_2$)

1.45 (9H, s, $-C(CH_3)_3$)

2.18 (2H, s, $-CH_2N<$)

-continued 2.26 (3H, s, $-COCH_3$)

2.45 (4H, br-t, 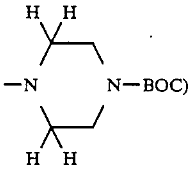 )

3.39 (4H, br-t, 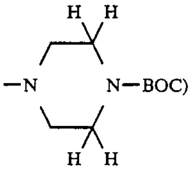 )

3.45 (2H, s, $-COCH_2CO-$)

3.95 (2H, s, $-CO_2CH_2-$)

REFERENCE EXAMPLE 6

Synthesis of 3-(4-formyl-1-piperazinyl)-2,2-dimethylpropyl acetoacetate

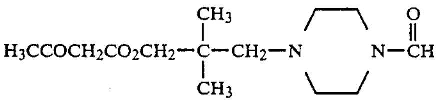

3-(4-Formyl-1-piperazinyl)-2,2-dimethylpropanol as the starting material was treated in the same manner as in Reference example 5 to give the subject compound (yield: 98%). The IR and NMR data of the compound thus obtained are as follows:

I R (Neat, $cm^{-1}$) 1735, 1710, 1675

$^1H$-NMR ($CDCl_3$, δ value)

0.91 (6H, s, $>C(CH_3)_2$)

2.23 (2H, s, $-CH_2N<$)

2.27 (3H, m, $-COCH_3$)

2.51 (4H, m, —CO— 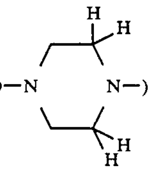 )

3.40 (4H, m, —CO— 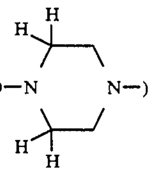 )

3.47 (2H, s, $-COCH_2CO-$)

3.95 (2H, s, $-CO_2CH_2-$)

-continued 7.96 (1H, br-s, >NCHO)

REFERENCE EXAMPLE 7

Synthesis of 3-(1-piperazinyl)-2,2-dimethylpropyl methyl 2,6-dimethyl-4-(m-nitrophenyl)-1,4-dihydropyridine-3,5-dicarboxylate

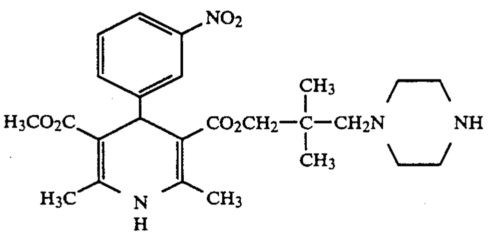

9.7 g of 3-[4-(tert-butyloxycarbonyl)-1-piperazinyl]-2,2-dimethylpropyl methyl 2,6-dimethyl-4-(m-nitrophenyl)-1,4-dihydropyridine-3,5-dicarboxylate was dissolved in ethanol and 50 ml of an ethanol solution of 9.9N hydrogen chloride was added under cooling with ice. After stirring the mixed solution for 1 hour under cooling with ice, isopropyl ether was added. The solid which separated was collected by filtration, dissolved in saturated aqueous sodium bicarbonate and extracted with ethyl acetate. The solvent was evaporated under reduced pressure and acetone was added to the residue. The crystal which separated was collected by filtration to give 3.5 g of the subject compound (yield: 43%). The IR and NMR data of the compound thus obtained are as follows:

I R (Nujol, $cm^{-1}$) 3270, 3220, 1690, 1520
$^1$H-NMR ($CDCl_3$, δ value)

0.81 (6H, s, >C($CH_3$)$_2$)

2.15 (2H, s, —$CH_2$N<)

2.32 (3H, s, =C—$CH_3$)

2.40 (3H, s, =C—$CH_3$)

2.70 (4H, br-t, 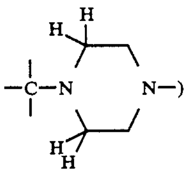

3.05 (4H, br-t, 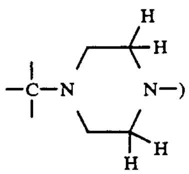

-continued 3.66 (3H, s, —$CO_2CH_3$)
3.78 (2H, s, —$CO_2CH_2$—)
5.08 (1H, s, $C_4$—H)

7.2~8.3 (6H, m, phenyl, >NH)

REFERENCE EXAMPLE 8

Synthesis of 3-(1-piperazinyl)-2,2-dimethylpropyl methyl 2,6-dimethyl-4-(m-nitrophenyl)-1,4-dihydropyridine-3,5-dicarboxylate

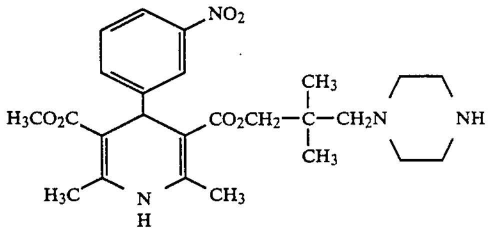

460 mg of 3-(4-formyl-1-piperazinyl)-2,2-dimethylpropyl methyl 2,6-dimethyl-4-(m-nitrophenyl)-1,4-dihydropyridine-3,5-dicarboxylate was dissolved in 1.5 ml of methanol and 0.3 ml of an ethanol solution of 9.9H hydrogen chloride was added. After stirring the mixed solution for one night, isopropyl ether was added. The solid which separated was collected by filtration, dissolved in saturated aqueous sodium bicarbonate and extracted with ethyl acetate. After washing with saturated solution of sodium chloride, the extract was dried with anhydrous sodium sulfate; then, the solvent was evaporated under reduced pressure to give 350 mg of the subject compound (yield: 81%).

REFERENCE EXAMPLE 9

Synthesis of 3-(4-allyl-1-piperazinyl)-2,2-dimethylpropanal

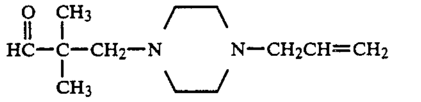

1-Allylpiperazine as the starting material was treated in the same manner as in Reference example 1 to give the subject compound (yield: 75%). The IR and NMR data of the compound thus obtained are as follows:

I R (Neat, $cm^{-1}$) 1720
$^1$H-NMR ($CDCl_3$, δ value)

1.00 (6H, s, >C($CH_3$)$_2$)

2.3~2.7 (10H, br, 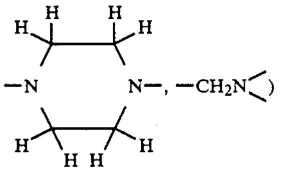

-continued 2.95 (2H, d, J=6Hz, $-CH_2-CH_2$)
4.9~6.0 (3H, m, vinyl)
9.55 (1H, s, —CHO)

REFERENCE EXAMPLE 10

Synthesis of 3-(4-allyl-1-piperazinyl)-2,2-dimethylpropanol

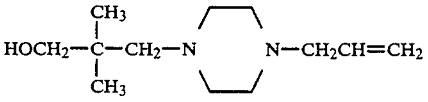

3-(4-Allyl-1-piperazinyl)-2,2-dimethylpropanal as the starting material was treated in the same manner as in Reference example 3 to give the subject compound (yield: 98%). The IR and NMR data of the compound thus obtained are as follows:

1 R (Neat, $cm^{-1}$) 3450
$^1$H-NMR ($CDCl_3$, δ value)

0.98 (6H, s, $>C(CH_3)_2$)

2.2~2.7 (10H, br, 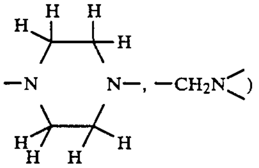)

2.95 (2H, d, J=6Hz, $-CH_2-CH=$)
3.50 (2H, s, $-CH_2OH$)
3.70 (1H, br, —OH)

REFERENCE EXAMPLE 11

Synthesis of 3-(4-allyl-1-piperazinyl)-2,2-dimethylpropyl acetoacetate

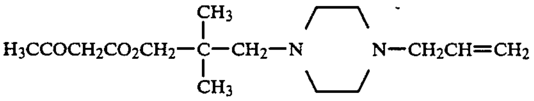

3-(4-Allyl-1-piperazinyl)-2,2-dimethylpropanol as the starting material was treated in the same manner as in Reference example 5 to give the subject compound (yield: 97%). The IR and NMR data of the compound thus obtained are as follows:

IR (Neat, $cm^{-1}$) 1740, 1720
$^1$H—NMR ($CDCl_3$, δ value)
0.90 (6H, s, $>C(CH_3)_2$)
2.28 (3H, s, $-COCH_3$)

2.4~2.7 (10H, br, 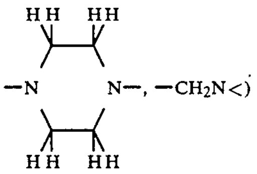)

-continued 3.00 (2H, d, J=6Hz, $-CH_2-CH=$)

3.45 (2H, s, $-COCH_2CO-$)
4.15 (2H, s, $-CO_2CH_2-$)
5.0~6.0 (3H, m, vinyl)

We claim:

1. A pharmaceutically-acceptable 1,4-dihydropyridine derivative represented by the formula:

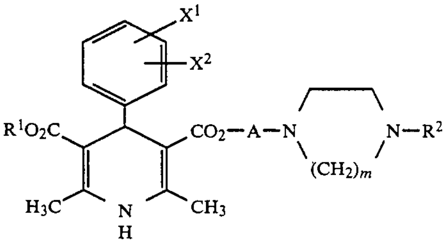

wherein each of $X^1$ and $X^2$ is, independently, hydrogen (—H), fluoromethyl, fluoromethoxy, halo, cyano or nitro;

$R^1$ is lower alkyl or cycloalkyl;

$R^2$ is acyl, alkoxycarbonyl, acylalkyl, an N-alkyl-substituted carbamoyalkyl, alkoxyalkyl, alkoxycarbonylalkyl, acyloxyalkyl, nitratoalkyl, cyanoalkyl, heterocycloalkyl, haloalkyl, alkenyl, or alkynyl; each acyl, including acyl of acylalkyl and acyl of acyloxyalkyl, being a carboxylic acid acyl;

A represents an alkylene having a carbon atom of which 2 alkyls are bonded and having a total of at least 5 carbon atoms;

m is an integer 1, 2 or 3; and wherein each acyl is an aliphatic acyl, an aromatic acyl or a heterocyclic acyl; each alkyl and each alkoxy, has from 1 to 5 carbon atoms; each alkenyl and each alkynyl has from 2 to 5 carbon atoms; and each heterocycle has 5 or 6 ring members, any hereto atom of which is a nitrogen atom or an oxygen atom; or a pharmacologically-acceptable acid-addition salt thereof.

2. A pharmaceutically-acceptable 1,4-dihydropyridine derivative as claimed in claim 1 wherein each heterocycle is piperidino or morpholino and A has from 5 to 10 carbon atoms.

3. The compound as claimed in claim 1 in which $R^2$ is acylalkyl, N-alkyl-substituted carbamoylalkyl, alkoxyalkyl, cyanoalkyl, heterocycle-alkyl, alkenyl or alkynyl.

4. The compound as claimed in claim 1 in which $R^2$ is alkenyl or alkynyl.

5. The compound as claimed in claim 1 in which A is an alkylene having in total not less than 5 and not more than 10 carbons.

6. The compound as claimed in claim 1, wherein the 1,4-dihydropyridine derivative is 2,2-Dimethyl-3-[4-(2-methyl-2-propenyl)-1-piperazinyl]propyl Methyl 1,4-Dihydro-2,6-dimethyl-4-(3-nitrophenyl)-3,5-pyridinedicarboxylate Dihydrochloride, 2,2-Dimethyl-3-[4-(2-butenyl)-1-piperazinyl]propyl Methyl 1,4-Dihydro-2,6-dimethyl-4-(3-nitrophenyl)-3,5-pyridinedicarboxylate Dihydrochloride, 2,2-Dimethyl-3-(4-cinnamyl-1-piperazinyl)propyl Methyl 1,4-Dihydro-2,6-dimethyl-4-(3-nitrophenyl)-3,5-pyridinedicarboxylate Dihydrochloride, 2,2-Dimethyl-3-[4-(2-butynyl)-1-piperazinyl]propyl Methyl 1,4-Dihydro-2,6-dimethyl-4-(3-nitrophenyl)-3,5-pyridinedicarboxylate Dihydrochloride, 2,2-Dimethyl-3-[4-(4-pentynyl)-1-piperazinyl]propyl Methyl 1,4-Dihydro-2,6-dimethyl-4-(3-nitrophenyl)-3,5-pyridinedicarboxylate Dihydrochloride, 2,2-Dimethyl-3-(4-piperidinoethyl-1-piperazinyl)propyl Methyl 1,4-Dihydro-2,6-dimethyl-4-(3-nitrophenyl)-3,5-pyridinedicarboxylate Trihydrochloride, 2,2-Dimethyl-3-[4-(2-hydroxyethyl)-1-piperazinyl]-propyl Methyl 1,4-Dihydro-2,6-dimethyl-4-(3-nitrophenyl)-3,5-pyridinedicarboxylate Dihydrochloride, 2,2-Dimethyl-3-(4-benzoyl-1-piperazinyl)propyl Methyl 1,4-Dihydro-2,6-dimethyl-4-(3-nitrophenyl)-3,5-pyridinedicarboxylate Hydrochloride, 2,2-Dimethyl-3-[4-(1-methyl-2-oxopropyl)-1-piperazinyl]propyl Methyl 1,4-Dihydro-2,6-dimethyl-4-(3-nitrophenyl)-3,5-pyridinedicarboxylate Dihydrochloride, 2,2-Dimethyl-3-[4-(2-cyanoethyl)-1-piperazinyl]propyl Methyl 1,4-Dihydro-2,6-dimethyl-4-(3-nitrophenyl)-3,5-pyridinedicarboxylate Dihydrochloride or 2,2-Dimethyl-3-[4-(2-furoyl)-1-piperazinyl]propyl Methyl 1,4-Dihydro-2,6-dimethyl-4-(3-nitrophenyl)-3,5-pyridinedicarboxylate Hydrochloride.

7. A pharmaceutical composition comprising from 0.1 to 100 mg per dosage unit of at least one compound selected from a 1,4-dihydropyridine derivative of claim 1 or a pharmacologically-acceptable acid addition salt thereof and one or more pharmaceutically-acceptable additives.

8. A pharmaceutical composition which is a calcium antagonist and comprises pharmaceutically-acceptable additive and an effective amount of a compound of claim 1.

9. A calcium antagonist pharmaceutical composition as claimed in claim 8 which is an antihypertensive agent, antianginal agent, cerebral circulation improving agent, peripheral circulation improving agent, renal function improving agent, antiarteriosclerosis drug, smooth muscle relaxant, antiallergic, therapeutic drug for cataract or therapeutic drug for glaucoma.

10. A pharmaceutical composition as claimed in claim 7 which is in the form of eye drops, nasal drops, inhalant, injectable or liniment.

11. In a method for treating or preventing a circulatory disease, an ischemic heart disease, a cerebral or peripheral circulatory disorder, or asthma by administering to a mammal in need of such therapy an effective amount of a compound useful for that purpose, the improvement wherein the compound is a 1,4-dihydropyridine derivative as claimed in claim 1, or a pharmacologically-acceptable acid-addition salt thereof.

* * * * *